United States Patent [19]

Hansen

[11] Patent Number: 4,469,254

[45] Date of Patent: Sep. 4, 1984

[54] CONTAINER WITH A DOSING CHAMBER

[76] Inventor: Gerhard Hansen, Heerstrasse 130, 7166 Sulzbach-Laufen, Fed. Rep. of Germany

[21] Appl. No.: 366,164

[22] Filed: Apr. 7, 1982

[30] Foreign Application Priority Data

Apr. 30, 1981 [DE] Fed. Rep. of Germany ... 8112834[U]

[51] Int. Cl.³ .................... B65D 37/00; G01F 11/26
[52] U.S. Cl. .................................. 222/207; 222/456; 222/541
[58] Field of Search ............... 222/202, 203, 206, 207, 222/212, 213, 215, 541, 424.5, 454, 456; 73/864.02; 215/31, 32, DIG. 3

[56] References Cited

U.S. PATENT DOCUMENTS

| | | | |
|---|---|---|---|
| 2,808,926 | 10/1957 | Drake et al. | 206/56 |
| 2,814,420 | 11/1957 | Elder, Jr. et al. | 222/215 |
| 3,303,847 | 2/1967 | Eaton | 222/215 X |
| 3,917,120 | 11/1975 | Larenz et al. | 222/129 |

FOREIGN PATENT DOCUMENTS

| | | |
|---|---|---|
| 425513 | 3/1935 | United Kingdom . |
| 1184065 | 3/1970 | United Kingdom . |
| 1214300 | 12/1970 | United Kingdom . |

*Primary Examiner*—Charles A. Marmor
*Assistant Examiner*—Michael S. Huppert
*Attorney, Agent, or Firm*—Walter C. Farley

[57] ABSTRACT

A dosing container for dispensing liquid medications or other liquids includes a compressible body portion and a tubular dosing chamber with an opening. The diameter of the dosing chamber is chosen on the basis of the liquid viscosity so that liquid will remain in the chamber when it is above the body. Annular grooves in the chamber walls improve its performance.

3 Claims, 3 Drawing Figures

CONTAINER WITH A DOSING CHAMBER

This invention relates to a container of the type intended to selectively dispense predetermined quantities or doses of a liquid containing therein, such as a medication.

BACKGROUND OF THE INVENTION

German Pat. No. 21 55 993 shows a known container of the general type with which the invention is concerned in which there is a narrow section between a dosing chamber and the compressible part of the container, which narrow section can be a constriction, a toothed gear-like or radial lamella arrangement, or the like. The narrow section is formed in such a way that the liquid medium can be introduced into the dosing chamber by a centrifugal motion. It has been found in practice that it is disadvantageous if it is necessary for the narrow section to be made with great accuracy since, with relatively slight changes in the cross section of the narrow section within usual tolerances, incorrect dosages often occur.

BRIEF DESCRIPTION OF THE INVENTION

An object of the present invention is to provide a dispensing container which considerably contributes to the reduction of the number of incorrect dosages.

Briefly described, the invention includes, in an improved plastic container for receiving a liquid and a gas and for selectively dispensing a measured quantity of the liquid, the container being of the type having a compressible body portion and an elongated dosing chamber coupled at one end to the body portion and having at the other end an openable orifice through which the liquid can be dispensed, the improvement wherein the inner diameter of the dosing chamber is selected as a function of the viscosity of the liquid contained therein such that the liquid remains in said chamber whenever said chamber is above the bottom of the body portion, and wherein the container further comprises an intermediate portion coupling the one end of the chamber to the body portion, the intermediate portion having step-wise increases in diameter from the chamber to the body portion such that, when said container is vertical, liquid flows from the intermediate portion into the body portion.

Because of the special construction of the dosing chamber and because of the elimination of the usual narrow section between the dosing chamber and the compressible body portion, accurate measuring is achieved in a simple fashion.

In addition, annular grooves can be provided in the chamber to achieve better containment of the liquid.

In order that the manner in which the foregoing and other objects are attained in accordance with the invention can be understood in detail, particularly advantageous embodiments thereof will be described with reference to the accompanying drawings, which form a part of this specification, and wherein.

Figure 1:
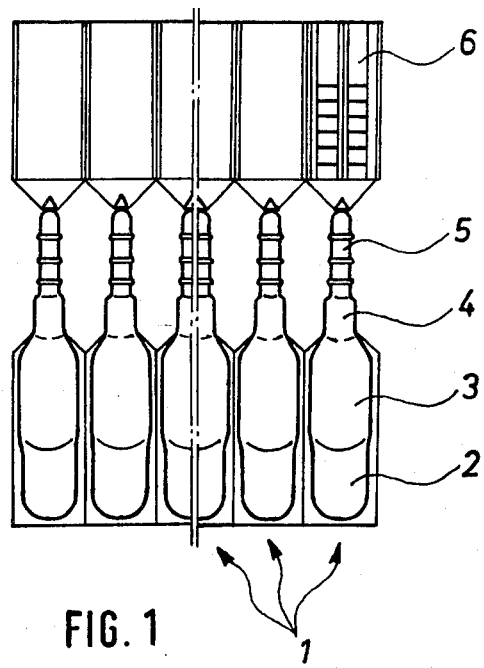
FIG. 1 is a foreshortened front elevation of a plurality of containers manufactured together, the containers illustrated being those for receiving a liquid medicinal agent.
Figure 2:
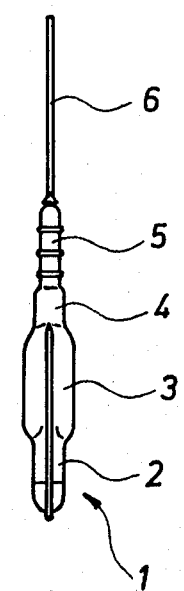
FIG. 2 is side elevation of the container assembly of FIG. 1.
Figure 3:
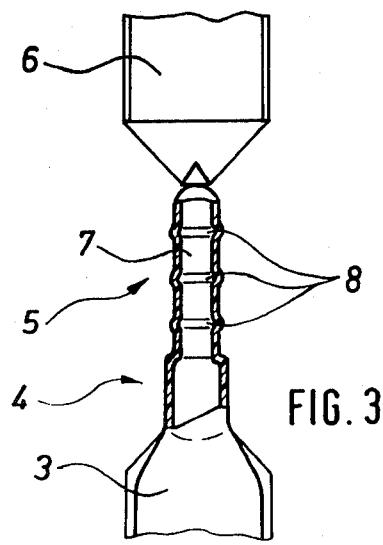
FIG. 3 is an enlarged partial front elevation of one of the containers of FIG. 1, partly in section.

Referring now to the drawings, each of the containers illustrated is made of an elastic or resilient, transparent substance. Normally, ten containers are produced concurrently in a blow-molding machine and are filled about halfway, preferably a little less than halfway, with a liquid medicinal substance, in the example to be described herein, and then are sealed. The remainder of the container is filled with air. Each container has a lower bottom part 2, a middle, prominent, flat and compressible container body part 3, a container neck 4, a measuring part 5, and a cap 6 which is designed to be breakable off of measuring part 5, at the end thereof opposite from body 2, to provide a dispensing orifice at one end of the measuring part.

The measuring part 5 has a dosing chamber 7 which is generally tubular in shape and has an essentially constant diameter. The diameter selected for dosing chamber 7 depends upon the viscosity of the medicine or other liquid in the container. The surface tension of the medicine must be sufficiently great that the amount of liquid in dosing chamber 7 remains there and does not flow back into the body portion when container 1 is held in the position shown in the drawing in which the break-off cap 6 is uppermost. Annular grooves 8 at uniform axial spacing are arranged in the dosing chamber 7 and define regions of slight radial enlargement. This contributes to the action of keeping the medicine in the dosing chamber.

The container neck 4 constitutes an intermediate portion which widens in step-wise fashion between the end of the dosing chamber opposite cap 6 and the body 3, and the diameter is such that any medicine remaining in container neck 4 can flow back into portions 2 or 3 when container 1 assumes the vertical position shown in the drawings.

In the example shown in the drawings, container 1 has volume of about 1.0 ml and contains nose drops as the medicinal agent in the amount of about 0.5 ml. The volume of dosing chamber 7 amounts to about 0.15 ml, so that at least two measured amounts, e.g., for the left and right nostrils, can be dispensed.

Other medicines that can be used with the container are ear to eye drops, or the like. It is also possible to use the container for some other liquid such as, for example, glue.

In order to use the medicine or other liquid contained within container 1, the container is held with the break-off cap down and the dosing chamber 7 is filled by lightly shaking the container. The container is then inverted and break-off cap 6 is broken off to open the dispensing orifice. The measuring part 5 can then be introduced into a nostril. By exerting pressure on body 3, the amount of medicine in dosing chamber 7 is forced into one of the nostrils. Then container 1 is again held with measuring part 5 downwardly and the dosing chamber is again filled by lightly shaking the container. After inverting the container 1, measuring part 5 is inserted into the other nostril and body 3 is pressed, dispensing the medication into the other nostril.

While one advantageous embodiment has been chosen to illustrate the invention it will be understood by those skilled in the art that various changes and modifications can be made therein without departing from the scope of the invention as defined in the appended claims.

What is claimed is:

1. In an improved flexible plastic container for receiving a liquid and a gas and for selectively dispensing a measured quantity of the liquid, the container being of the type having a compressible body portion, and an elongated dosing chamber coupled at one end to the body portion and having at the other end an openable orifice through which the liquid can be dispensed, the improvement wherein the inner diameter of the dosing chamber is selected as a function of the viscosity of the liquid contained therein such that the liquid remains in said chamber whenever said chamber is above the bottom of said body portion; and said container is formed in one piece;

and wherein said container further comprises an intermediate portion coupling said one end of said chamber to said body portion, said intermediate portion having an abrupt stepwise increase in diameter from said chamber, the transition between said chamber and said intermediate portion being substantially unobstructed and having a relatively sharp corner such that, when said container is vertical, liquid flows from said intermediate portion into said body portion.

2. A container according to claim 1 wherein said dosing chamber comprises means defining at least one radially outwardly extending annular groove.

3. A container according to claim 2 wherein said chamber includes a plurality of axially spaced grooves.

* * * * *